United States Patent
Ogawa

(10) Patent No.: US 10,555,786 B2
(45) Date of Patent: Feb. 11, 2020

(54) OPERATION INPUT DEVICE AND MEDICAL MANIPULATOR SYSTEM

(71) Applicant: OLYMPUS CORPORATION, Tokyo (JP)

(72) Inventor: Ryohei Ogawa, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 269 days.

(21) Appl. No.: 15/678,396

(22) Filed: Aug. 16, 2017

(65) Prior Publication Data

US 2017/0340399 A1 Nov. 30, 2017

Related U.S. Application Data

(63) Continuation of application No. PCT/JP2016/054843, filed on Feb. 19, 2016.

(30) Foreign Application Priority Data

Feb. 26, 2015 (JP) ................................. 2015-036056

(51) Int. Cl.
*A61B 34/00* (2016.01)
*A61B 34/35* (2016.01)
(Continued)

(52) U.S. Cl.
CPC .......... *A61B 34/71* (2016.02); *A61B 17/2833* (2013.01); *A61B 34/30* (2016.02);
(Continued)

(58) Field of Classification Search
CPC ......... A61B 34/30; A61B 34/35; A61B 34/37; A61B 34/70–77
See application file for complete search history.

(56) References Cited

U.S. PATENT DOCUMENTS

| 5,876,325 A | 3/1999 | Mizuno et al. |
| 7,806,891 B2 | 10/2010 | Nowlin et al. |

(Continued)

FOREIGN PATENT DOCUMENTS

| EP | 1520548 A2 | 4/2005 |
| EP | 2671686 A1 | 12/2013 |

(Continued)

OTHER PUBLICATIONS

International Search Report dated Apr. 19, 2016 issued in PCT/JP2016/054843.

(Continued)

*Primary Examiner* — Christopher A Flory
(74) *Attorney, Agent, or Firm* — Scully, Scott, Murphy & Presser, P.C.

(57) ABSTRACT

This operation input device is an operation input device for inputting an operating command to a manipulator for observing or treating an affected area. Provided is an operation input device including: a grip gripped by an operator with his/her hand; and an arm for movably supporting this grip, wherein this arm includes at least two link members, and at least one joint for linking a neighboring pair of the link members tiltably about joint axes intersecting the longitudinal axes thereof, and each of the joints includes: a sensor for detecting the relative angle displacement of each of the link members that are linked; and a friction generation section configured to generate a frictional torque in a direction opposite to the direction in which a torque is applied.

11 Claims, 10 Drawing Sheets

(51) Int. Cl.
*A61B 34/37* (2016.01)
*A61B 34/30* (2016.01)
*A61B 17/28* (2006.01)
*A61B 90/50* (2016.01)
*A61B 90/00* (2016.01)
*A61B 17/29* (2006.01)

(52) U.S. Cl.
CPC .............. *A61B 34/35* (2016.02); *A61B 34/37* (2016.02); *A61B 17/29* (2013.01); *A61B 2090/035* (2016.02); *A61B 2090/508* (2016.02)

(56) References Cited

U.S. PATENT DOCUMENTS

| | | | |
|---|---|---|---|
| 2005/0075536 A1 | 4/2005 | Otsuka et al. | |
| 2005/0165415 A1* | 7/2005 | Wales | A61B 17/07207 606/139 |
| 2006/0190034 A1* | 8/2006 | Nishizawa | A61B 17/29 606/205 |
| 2007/0208375 A1* | 9/2007 | Nishizawa | A61B 17/29 606/205 |
| 2009/0163929 A1* | 6/2009 | Yeung | B25J 9/047 606/130 |
| 2010/0121347 A1* | 5/2010 | Jaspers | A61B 34/71 606/130 |
| 2011/0298309 A1 | 12/2011 | Kim et al. | |
| 2012/0138660 A1* | 6/2012 | Shelton, IV | A61B 17/115 227/176.1 |
| 2012/0191107 A1* | 7/2012 | Tanner | A61B 6/12 606/130 |
| 2012/0191245 A1* | 7/2012 | Fudaba | B25J 3/04 700/254 |
| 2012/0209291 A1* | 8/2012 | Anderson | A61B 90/57 606/130 |
| 2012/0221145 A1 | 8/2012 | Ogawa | |
| 2012/0310256 A1* | 12/2012 | Brisson | A61B 34/77 606/130 |
| 2013/0030569 A1* | 1/2013 | Fudaba | G05B 19/423 700/245 |
| 2013/0184871 A1* | 7/2013 | Fudaba | B25J 13/02 700/264 |
| 2013/0197492 A1* | 8/2013 | Kishi | A61B 17/00 606/1 |
| 2013/0296882 A1* | 11/2013 | Kim | A61B 34/70 606/130 |
| 2013/0297072 A1* | 11/2013 | Fudaba | B25J 3/04 700/260 |
| 2014/0018821 A1* | 1/2014 | Yeung | B25J 9/047 606/130 |
| 2014/0114477 A1* | 4/2014 | Sato | B25J 9/1664 700/250 |
| 2014/0137669 A1* | 5/2014 | Sato | A61B 6/12 73/862.321 |
| 2014/0155906 A1* | 6/2014 | Pratt | A61B 17/8869 606/103 |
| 2014/0172143 A1* | 6/2014 | Fudaba | B25J 9/1656 700/108 |
| 2014/0195010 A1* | 7/2014 | Beira | A61B 17/00234 700/3 |
| 2014/0288525 A1* | 9/2014 | Fudaba | A61B 5/066 604/500 |
| 2015/0090065 A1 | 4/2015 | Kishi | |
| 2015/0142014 A1 | 5/2015 | Hyodo et al. | |
| 2015/0245873 A1* | 9/2015 | Hong | A61B 17/00234 606/130 |
| 2016/0135907 A1 | 5/2016 | Murata | |
| 2016/0235408 A1* | 8/2016 | Shelton, IV | A61B 17/07207 |
| 2016/0262745 A1* | 9/2016 | Morgan | A61B 17/072 |
| 2017/0007250 A1* | 1/2017 | Shelton, IV | A61B 17/07207 |
| 2017/0100197 A1* | 4/2017 | Zubiate | A61B 17/3417 |
| 2018/0303482 A1* | 10/2018 | Shelton, IV | A61B 17/07207 |
| 2018/0317918 A1* | 11/2018 | Shelton, IV | A61B 17/07207 |
| 2019/0105039 A1* | 4/2019 | Morgan | A61B 17/072 |
| 2019/0117224 A1* | 4/2019 | Setser | A61B 17/07207 |

FOREIGN PATENT DOCUMENTS

| | | |
|---|---|---|
| EP | 2862680 A1 | 4/2015 |
| EP | 2 881 049 A1 | 10/2015 |
| EP | 3 025 830 A1 | 1/2016 |
| JP | H08-150578 A | 6/1996 |
| JP | 2005-125056 A | 5/2005 |
| JP | 2007-098507 A | 4/2007 |
| JP | 2011-255493 A | 12/2011 |
| JP | 2012-055985 A | 3/2012 |
| JP | 2012-171088 A | 9/2012 |
| JP | 2013-255966 A | 12/2013 |
| JP | 2014-023821 A | 2/2014 |
| JP | 2015-024456 A | 2/2015 |
| WO | 2014/021218 A1 | 2/2014 |
| WO | 2015/012051 A1 | 1/2015 |

OTHER PUBLICATIONS

Extended Supplementary European Search Report dated Oct. 19, 2018 in European Patent Application No. 16 75 5360.1.

\* cited by examiner

FRICTIONAL TORQUE IS LARGE

FRICTIONAL TORQUE IS SMALL

OPERATION INPUT DEVICE AND MEDICAL MANIPULATOR SYSTEM

CROSS-REFERENCE TO RELATED APPLICATIONS

This application is a Continuation Application of International Application No. PCT/JP2016/054843 filed on Feb. 19, 2016, which claims priority to Japanese Application No. 2015-036056 filed on Feb. 26, 2015. The contents of International Application No. PCT/JP2016/054843 and Japanese application No. 2015-036056 are hereby incorporated herein by reference in their entirety.

TECHNICAL FIELD

The present invention relates to an operation input device and a medical manipulator system.

BACKGROUND ART

There is a known surgical manipulator system provided with: a multi-joint operating section that is operated by an operator to input a motion command; and a multi-joint manipulator that moves on the basis of the motion command input through the operation of this operating section (refer to, for example, PTL 1).

In this PTL 1, the operating section and the manipulator can be connected and disconnected, and each of the joints of the operating section is provided with a motor. While the operating section and the manipulator are disconnected, a deviation caused between the operating section and the manipulator that are disconnected is prevented by locking each of the joints of the operating section using the motor.

CITATION LIST

Patent Literature

{PTL 1}
U.S. Pat. No. 7,806,891

SUMMARY OF INVENTION

An aspect of the present invention provides an operation input device for inputting an operating command to a manipulator for observing or treating an affected area, the operation input device comprising: a grip that is gripped by a hand of an operator; and an arm which includes at least two link members and at least one joint for linking a neighboring pair of the link members so that they can tilt about a joint axis intersecting longitudinal axes thereof, and which movably supports the grip, wherein each of the joints includes: a shaft that is fixed to one of the pair of link members and that extends along the joint axis; a spring that is fixed to the other of the pair of link members and that is wound around an outer circumferential surface of the shaft to tighten the shaft radially inward; and a shaft unit that includes the shaft and the spring configured to generate a frictional torque in an opposite direction to a direction in which a torque is applied.

DESCRIPTION OF EMBODIMENTS

An operation input device 2 and a medical manipulator system 1 according to an embodiment of the present invention will now be described with reference to the drawings.

Figure 1:
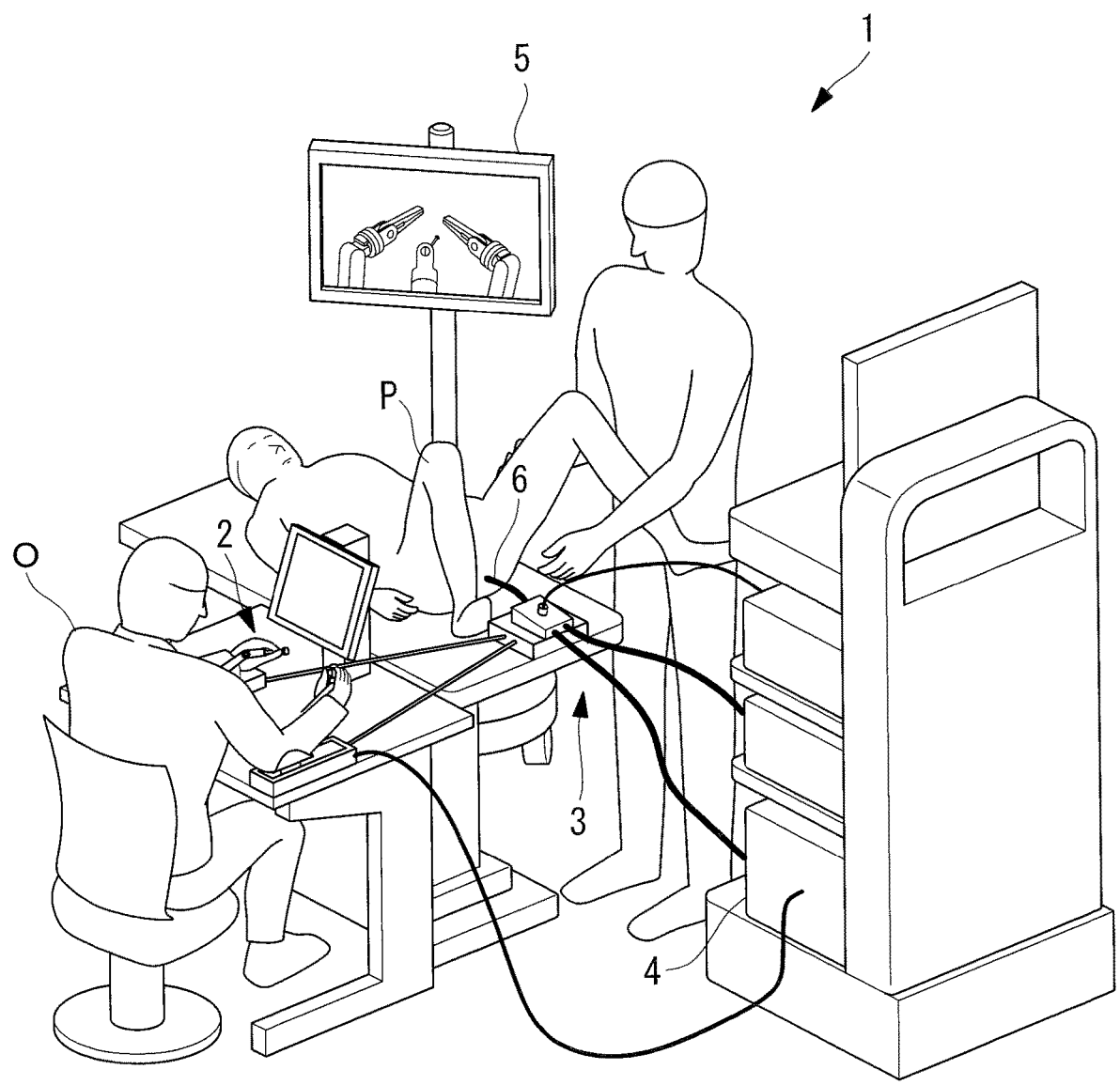
FIG. 1 is an overall structure diagram showing a medical manipulator system provided with an operation input device according to an embodiment of the present invention.

As shown in FIG. 1, the medical manipulator system 1 according to this embodiment includes: the operation input device 2 operated by an operator O; manipulators 3 inserted into a body cavity of a patient P; a control unit 4 for controlling the manipulators 3 on the basis of the operation of the operation input device 2; and a monitor 5.

Figure 2:
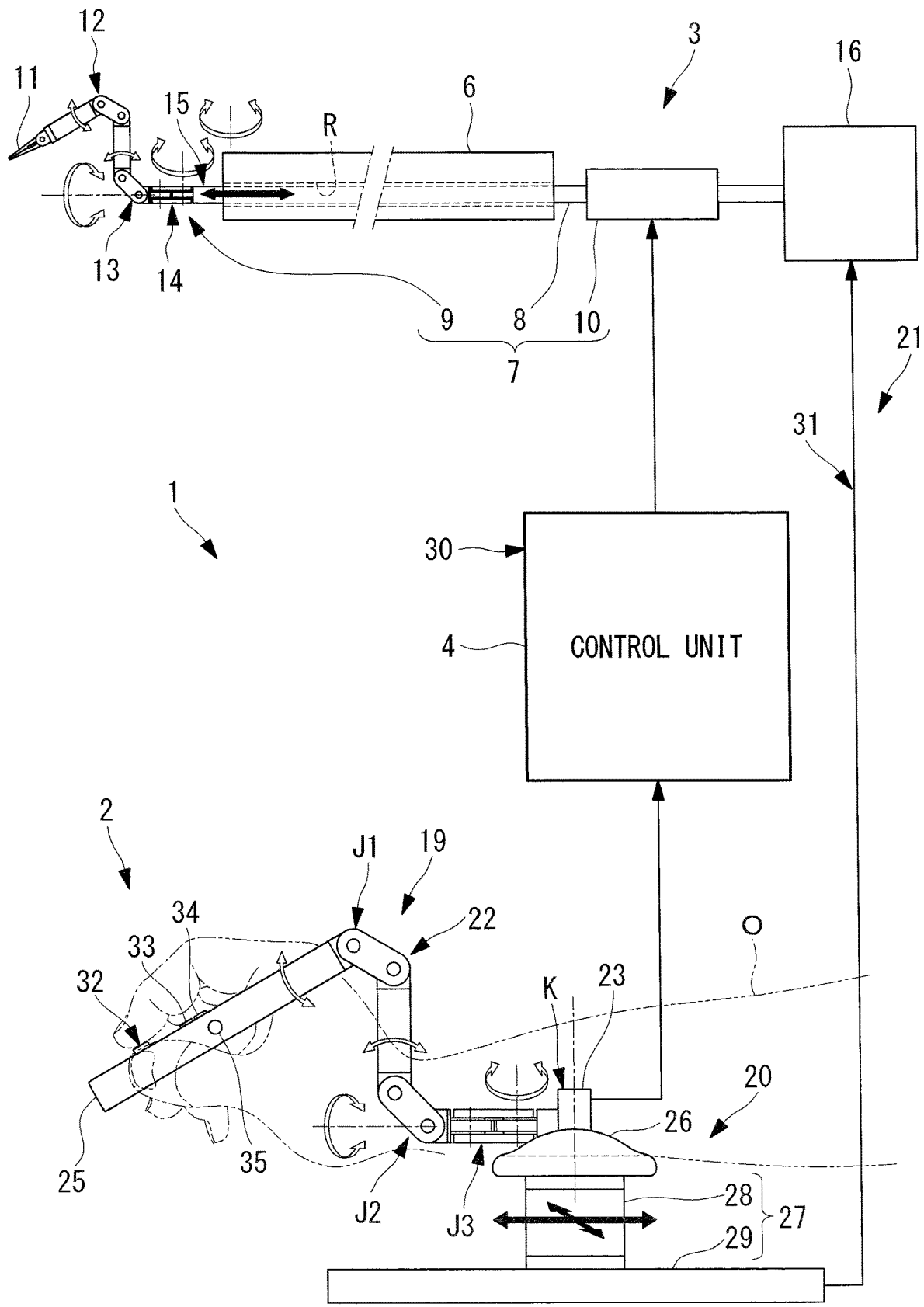
FIG. 2 is a diagram showing a manipulator, the operation input device, and a control unit used in the medical manipulator system in FIG. 1.

As shown, for example, in FIG. 2, each of the manipulators 3 includes: an insertion section 6 inserted into the body cavity of the patient P; and a distal end side moving section 7 that is inserted into the body of the patient P through a channel R formed so as to pass through in the longitudinal direction of this insertion section 6. Each of the distal end side moving sections 7 includes: an elongated section 8 disposed in the channel R movably in the longitudinal direction; a movable section 9 provided at a distal end of this elongated section 8; a high frequency gripper 11 provided at a distal end of the movable section 9; and a distal-end driving unit 10 that is disposed on the proximal end side of the elongated section 8 and that drives the movable section 9 by means of a force transmission member, such as a wire, which is not shown in the figure. The distal-end driving unit 10 includes an electrical drive source (not shown in the figure), such as a motor, for imparting tension to the wire according to a motion command from the control unit 4.

Each of the movable sections 9 has: three joints 12, 13, and 14 for tilting a treatment section 11, such as a gripping forceps, disposed at the distal end about an axis orthogonal to the longitudinal axis of the elongated section 8; and one joint 15 for rotating the treatment section 11 about the longitudinal axis of the elongated section 8, as indicated by the outlined white arrows in FIG. 2. Each of the movable sections 9 can set a three-dimensional position of the distal end of each of the gripping forceps 11 through motion of these four joints 12, 13, 14, and 15.

In addition, the manipulators 3 include two proximal end side moving sections 16 that are connected to the proximal end sides of the distal end side moving sections 7, that advance/withdraw the distal end side moving sections 7 in the longitudinal directions of the insertion sections 6, and that bend the elongated sections 8 in directions orthogonal to the longitudinal directions in the vicinity of the distal ends of the insertion sections 6.

Figure 3:
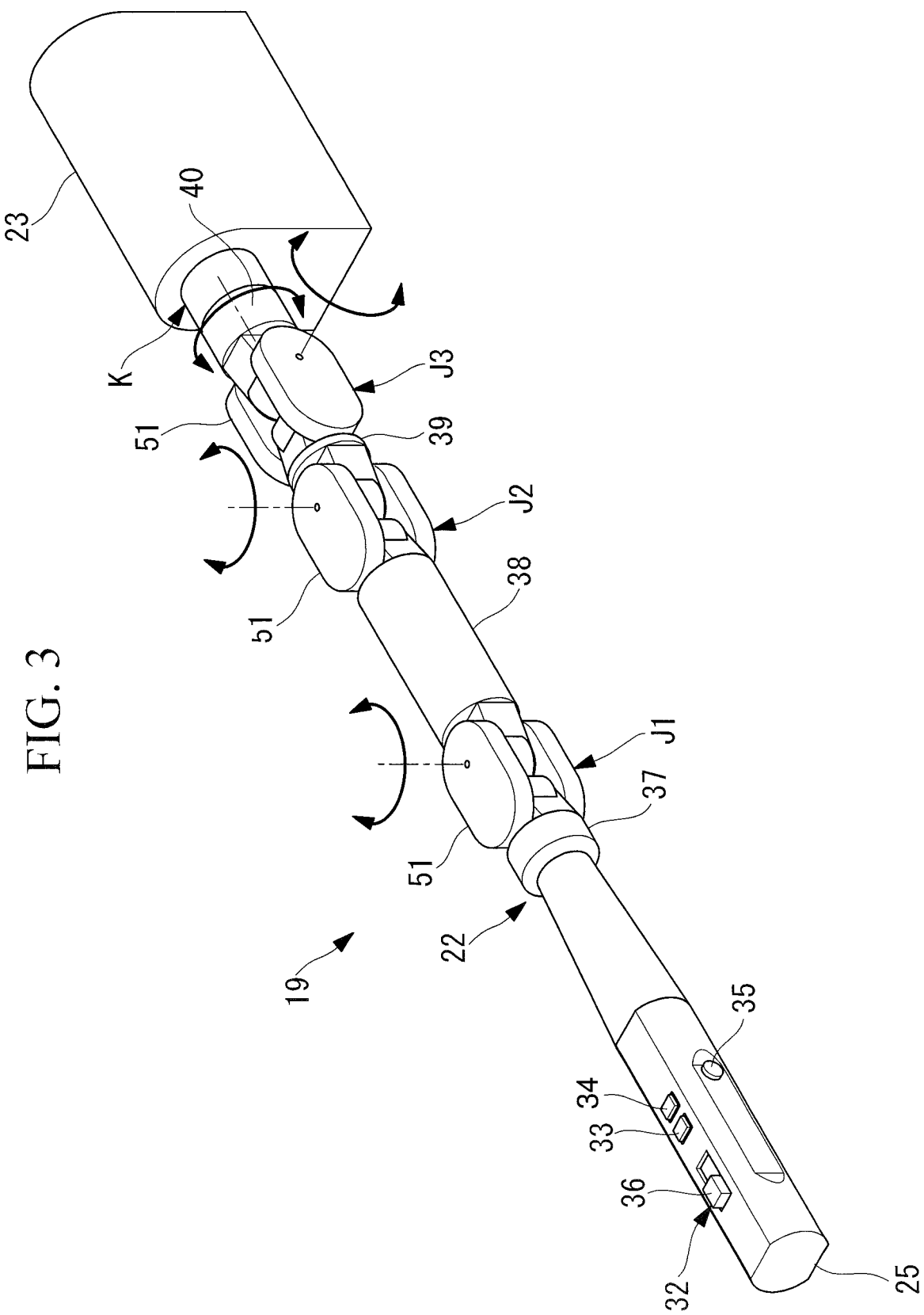
FIG. 3 is a perspective view showing the operation input device provided in the medical manipulator system in FIG. 1.

As shown in FIGS. 2 and 3, the operation input device 2 according to this embodiment includes: first operating sections 19 that are gripped and operated by the operator O with his/her hands; second operating sections 20 that are operated by the operator O with his/her wrists or arms; and a command transmission unit 21 for transmitting, to the manipulators 3, operating commands input with these operating sections 19 and 20.

Each of the first operating sections 19 is configured to have a shape similar to that of the movable section 9 of the manipulator 3 and includes: a grip section 25 gripped by the operator O with his/her hand; an arm section 22 for supporting the grip section 25 with joints J1, J2, J3, and K whose number of joints is the same as that of the movable section 9; and a body section 23 for supporting this arm section 22.

As shown in FIGS. 2 and 3, the grip section 25 is formed in a rod shape that is gripped by the operator O and includes a slide sensor 32 and three push buttons 33, 34, and 35 on the outer circumferential surface thereof.

The slide sensor 32 is provided slidably in a longitudinal axis direction of the rod-shaped grip section 25 and is used to adjust the open/close angle of the gripper, which is one of the main functions of the high frequency gripper 11 serving as an end effector. The slide sensor 32 includes a slidable slider 36. The slider 36 is disposed at a position where it can easily be operated by the operator O with the pointing finger of his/her hand gripping the grip section 25, and when the pointing finger releases the slider 36, it is kept unmoving at that position.

Among the three push buttons 33, 34, and 35, the two push buttons 33 and 34 are arranged side by side in a slide direction of the slider 36 of the slide sensor 32. These push buttons 33 and 34 are on/off switches for performing high frequency energization from the gripper, which is another main function of the high frequency gripper 11 serving as the end effector. The two push buttons 33 and 34 are selectively pressed for use at the time of treatment in, for example, an incision mode or a coagulation mode.

The other push button 35 is disposed at a position shifted in the circumferential direction of the grip section 25 by 90° from, for example, the slide sensor 32. This push button 35 is, for example, a clutch button and can switch between connection and disconnection of the interlinked movement between the operation input device 2 and the manipulator 3 each time it is pressed.

The arm section 22 includes: four link members 37, 38, 39, and 40; three joints J1, J2, and J3 for linking these four link members 37, 38, 39, and 40 in series; and the one rotational joint K for supporting the entirety of them in a manner allowing rotation thereof about the horizontal axis relative to the body section 23. The grip section 25 is fixed to the distal end of the most-distal-end link member 37.

Figure 4:
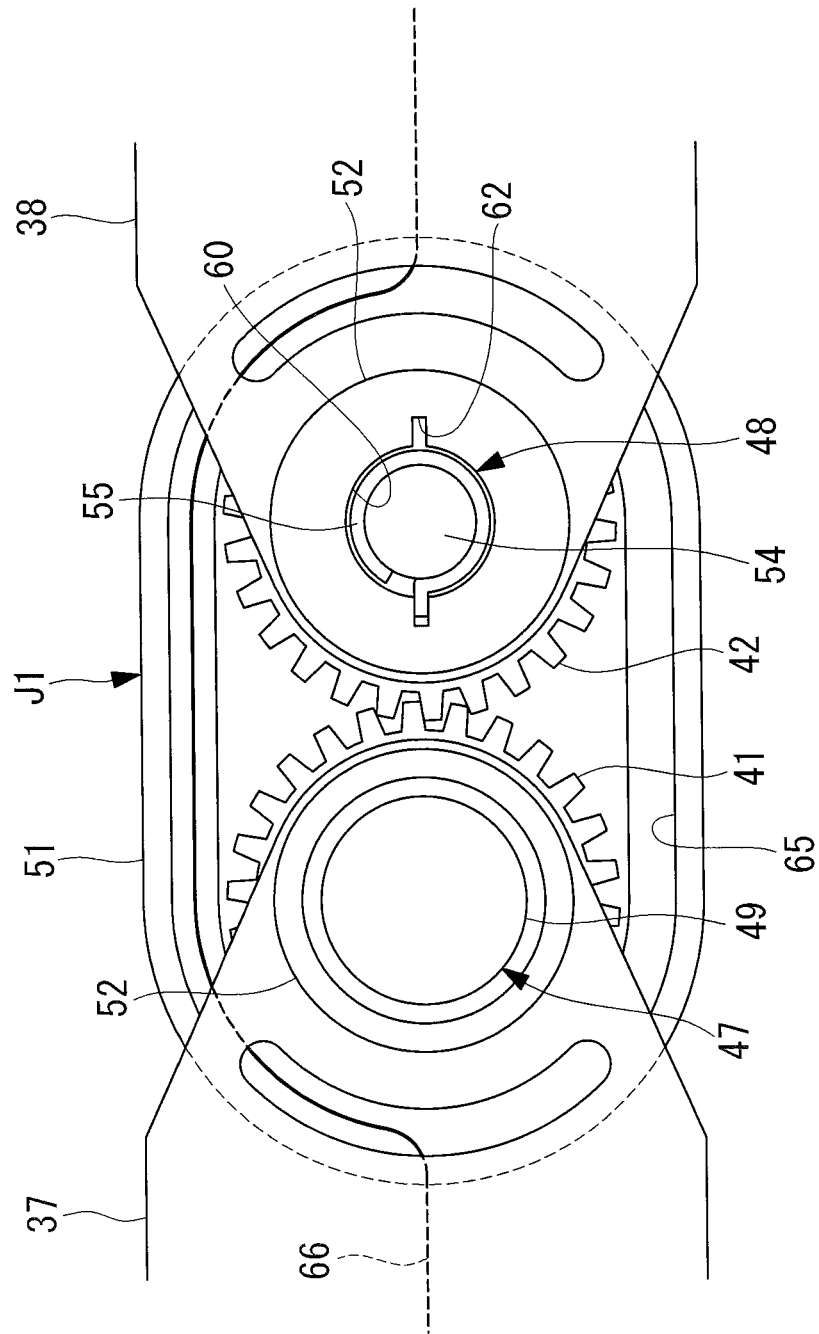
FIG. 4 is a plan view showing the internal structure of a joint of the operation input device in FIG. 3.
Figure 5:
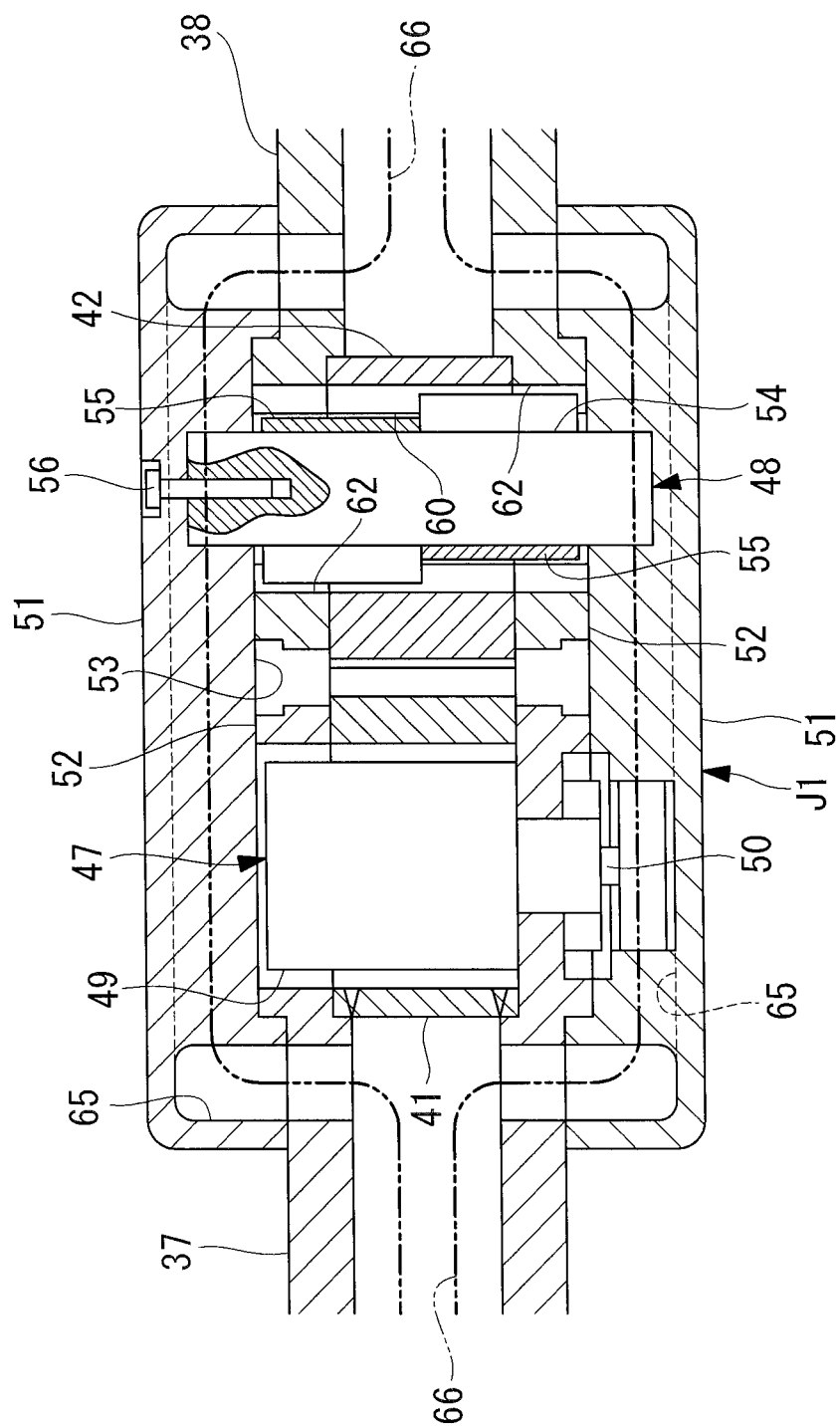
FIG. 5 is a longitudinal sectional view showing the internal structure of the joint of the operation input device in FIG. 3.

Because the three joints J1, J2, and J3 on the distal end side have the same structure, a description will be given of the joint J1 as an example. As shown in FIGS. 4 and 5, the joint J1 includes spur wheels (gears) 41 and 42 that are fixed to the two neighboring link members 37 and 38, respectively, and that mesh with each other; and joining members 51 that are attached to the two link members 37 and 38, respectively, to link the two link members 37 and 38 so as to be capable of tilting about the parallel axes of these two spur wheels 41 and 42.

The two spur wheels 41 and 42 fixed to the two link members 37 and 38, respectively, are kept meshing with each other at all times by the joining members 51. Therefore, the joint J1 is configured to work with a relationship in which, when the relative angle between the two link members 37 and 38 linked by the joint J1 is changed, the tilting angles of the joining member 51 relative to the one link member 37 and the tilting angle of the other link member 38 relative to the joining member 51 are equal to one half of the relative angle between the two link members 37 and 38. By doing so, the joint J1 constitutes a joint having a so-called double-joint structure, in which the two link members 37 and 38 are swiveled about the two axis.

If it is assumed that, for example, the link member 37 disposed on the distal end side is a first link member and the link member 38 disposed on the proximal end side is a second link member, an angle sensor (sensor) 47 is disposed at an axial position of the spur wheel 41 fixed to the first link member 37 and a shaft unit (friction generation section) 48 is disposed at an axial position of the spur wheel 42 fixed to the second link member 38.

The angle sensor 47 is an encoder, includes a sensor body 49 fixed to the first link member 37 and a detection shaft 50 fixed to the joining members 51, and detects the relative angles between the first link member 37 and the joining members 51. As described above, because the relative angle displacements between the link member 37 and the joining members 51 are just one half of the relative angle displacement between the first link member 37 and the second link member 38, the angle sensor 47 indirectly detects the relative angle displacement between the two link members 37 and 38 as one half thereof.

Figure 6:
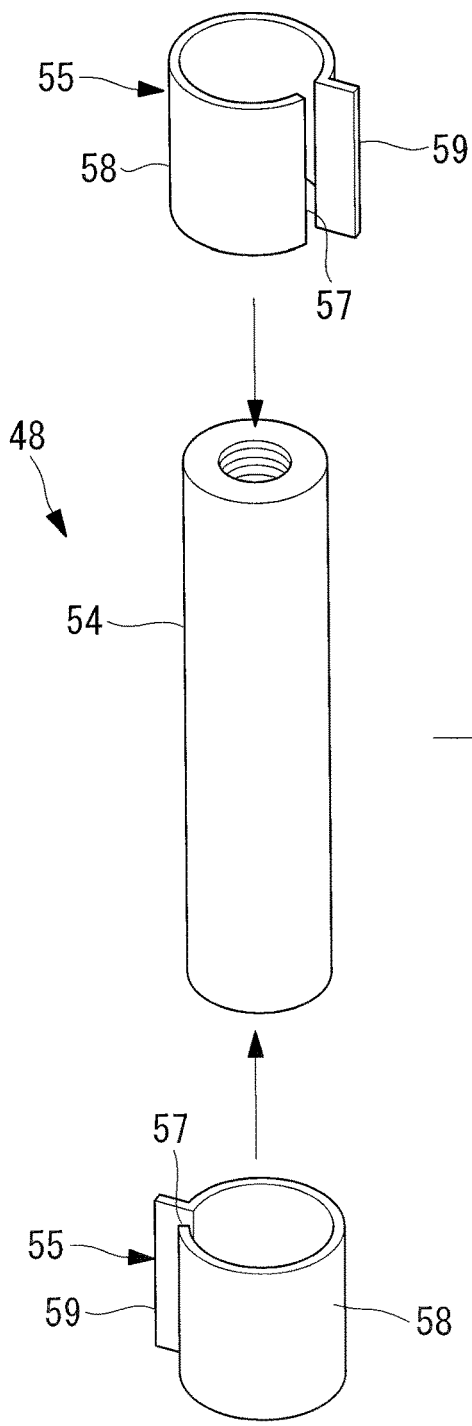
FIG. 6($a$) illustrates an exploded perspective view of a shaft unit provided in the joint of the operation input device in FIG. 3 and FIG. 6($b$) illustrates a perspective view showing insertion of the shaft unit into an insertion hole.
Figure 6:
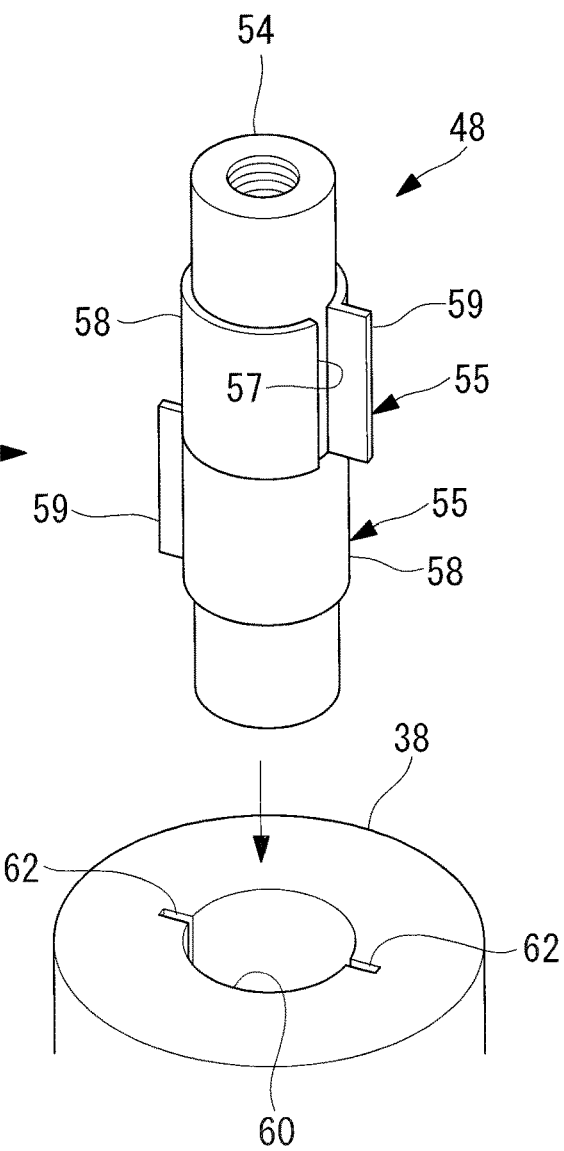

As shown in FIG. 6(a), the shaft unit 48 includes: a shaft member 54 fixed to the joining members 51; and a pair of plate spring members (springy members) 55 that are wound around the outer circumferential surface of this shaft member 54 to tighten this shaft member 54 radially inward.

The shaft member 54 is fixed to a joining member 51 with a screw 56 as shown in FIG. 5.

Each of the plate spring members 55 includes: a cylindrical tightening section 58 having a slit 57; and a projecting section 59 that is formed by bending, radially outward, one end of the tightening section 58 in the circumferential direction thereof such that the one end protrudes. The inner diameter of the tightening section 58 in a free state is set to be smaller than the outer diameter of the shaft member 54. When the plate spring member 55 is to be mounted on the shaft member 54, the shaft member 54 is made to tightly fit to the inner side of the tightening section 58 while elastically deforming the tightening section 58 so as to push the slit 57 wide against the resilience force. By doing so, the tightening section 58 of the plate spring member 55 is wound around the outer circumferential surface of the shaft member 54, whereby the plate spring member 55 is mounted so as to tighten the shaft member 54 radially inward.

As shown in FIG. 6(b), the pair of plate spring members 55 provided in the shaft unit 48 are mounted on the shaft member 54 such that the directions in which the tightening sections 58 are wound and extend with respect to the respective projecting sections 59 thereof differ from each other.

Figure 7A:
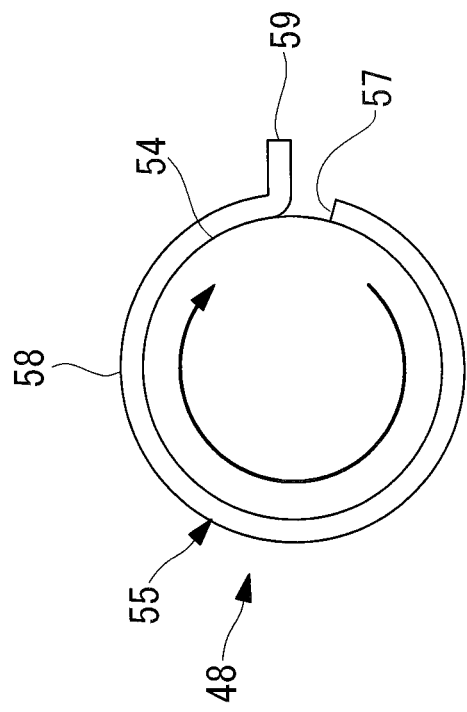
FIGS. 7($a$) and 7($b$) are plan views of the shaft unit in FIGS. 6($a$) and 6($b$), with FIG. 7($a$) illustrating a rotational direction of a shaft member in which a large frictional torque is generated and FIG. 7($b$) illustrating a rotational direction of the shaft member in which a small frictional torque is generated.

When the situation where the tightening section 58 is wound, for example, counterclockwise around the outer circumferential surface of the shaft member 54, if the plate spring member 55 is fixed and a torque that turns the shaft member 54 counterclockwise is applied, as shown in FIG. 7(a), then the tightening section 58 is pulled in a direction in which the slit 57 becomes narrower by the friction between the outer circumferential surface of the shaft member 54 and the inner surface of the tightening section 58, thereby increasing the frictional torque.

Figure 7B:
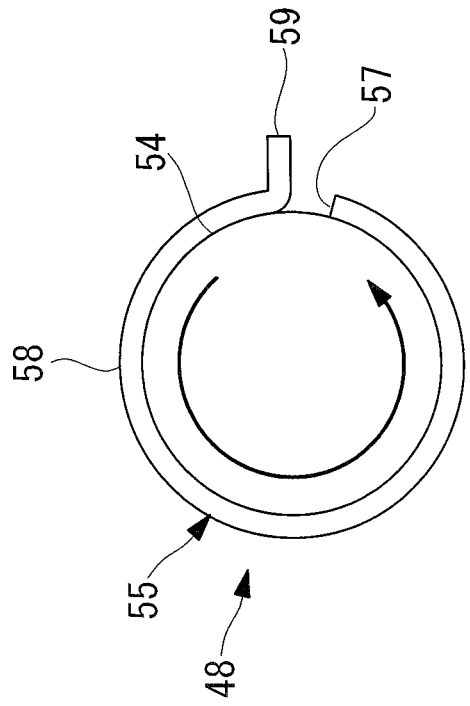

In contrast, if the plate spring member 55 is fixed and a torque that turns the shaft member 54 clockwise is applied, as shown in FIG. 7(b), then the tightening section 58 is pulled in a direction in which the slit 57 becomes wider by the friction between the outer circumferential surface of the shaft member 54 and the inner surface of the tightening section 58, thereby decreasing the frictional torque.

Thus, as a result of the pair of plate spring members 55 being mounted on the same shaft member 54 so as to be wound in directions different from each other, the frictional torque increases by either of the plate spring members 55, in whichever of the clockwise and counterclockwise directions the shaft member 54 turns.

made for an example of the joint J1, the shaft unit 48 is inserted into an insertion hole 60 that passes through the second link member 38 and is fixed with the screw 56 to at least one of the two joining members 51, which are detachably attached so as to sandwich the first and second link members 37 and 38 from both sides in the axial directions of the spur wheels 41 and 42, as shown in FIGS. 5 and 6(b). As shown in FIG. 6(b), the insertion hole 60 formed in the second link member 38 is provided with grooves 62 formed along the longitudinal direction at two positions with a circumferential gap therebetween.

Each of the grooves 62 has a groove width substantially identical to the thickness of the plate spring member 55, and the grooves 62 accommodate the two projecting sections 59 of the pair of plate spring members 55, respectively, when the shaft unit 48 is inserted into the insertion hole 60. More specifically, the shaft member 54 and the pair of plate spring members 55 can be inserted into the insertion hole 60 and extracted from the insertion hole 60 in the form of the shaft unit 48.

Then, when the projecting sections 59 are accommodated in the grooves 62, the plate spring members 55 engage with the second link member 38 so as not to move in the circumferential directions of the tightening sections 58.

In addition, in this embodiment, the magnitudes of the frictional torques generated by the plate spring members 55 are set as follows.

Figure 8:
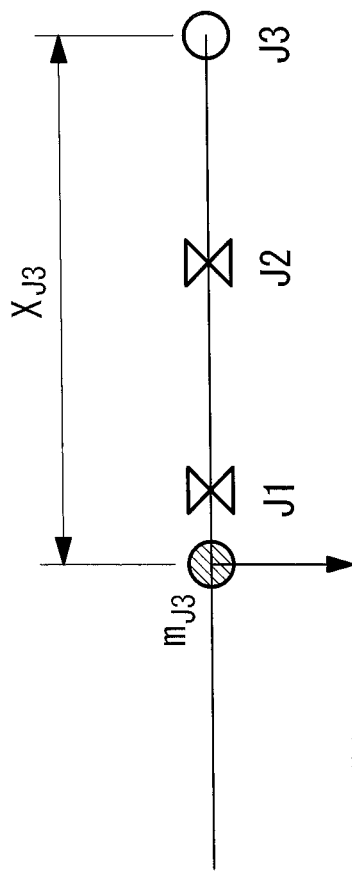
FIGS. 8($a$) and 8($b$) are schematic diagrams illustrating weight driven torques applied to the joint on the most proximal end side in FIG. 8($a$) and the two joints on the distal end side in FIG. 8($b$), provided in the operation input device in FIG. 3.
Figure 8:
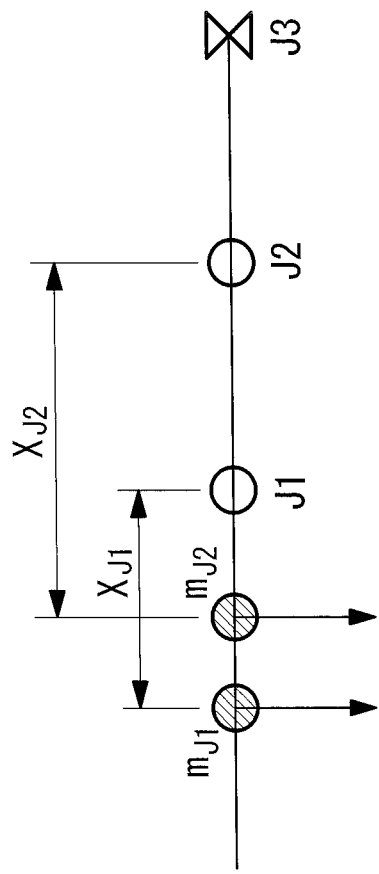

As shown in FIGS. 8(a) and 8(b), each of the joints J1, J2, and J3 constituting the arm section 22 is considered to receive a torque resulting from the sum of the weights of the link members 37, 38, and 39, the joints J1, J2, and J3, and the grip section 25 that are disposed towards the distal end side from the joints J1, J2, and J3 being applied to the combined center of gravity. Therefore, the frictional torque generated in each of the joints J1, J2, and J3 is set to have a magnitude exceeding the torque acting on each of the joints J1, J2, and J3 due to the above-described weights.

The torque due to the weights acting on each of the joints J1, J2, and J3 becomes largest in a state where the combined center of gravity is farthest from the joint J1, J2, or J3, namely, in a state where all the joints J1, J2, and J3 are extended.

As for the joint J3 disposed on the most proximal end side, the total weight $m_{J3}$ of the members 37, 38, and 39 disposed towards the distal end side from the joint J3 is applied to the combined center of gravity $x_{J3}$ as shown in FIG. 8(a), and hence, a torque $T_{J3}$ acting on the joint J3 is as follows.

$$T_{J3} = m_{J3} \times x_{J3}$$

As shown in FIG. 8(b), as for the two joints J1 and J2 disposed on the distal end side, the total weights $m_{J1}$ and $m_{J2}$ of the members 37 and 38 disposed towards the distal end side from the individual joints J1 and J2 are applied to the combined centers of the gravity $x_{J1}$ and $x_{J2}$, as shown in FIG. 8(b), and hence, the torques $T_{J1}$ and $T_{J2}$ acting on the joints J1 and J2 are as follows.

$$T_{J1} = m_{J1} \times x_{J1}$$

$$T_{J2} = m_{J2} \times x_{J2}$$

More specifically, for the pairs of plate spring members 55, the spring constants and the dimensions of the tightening sections 58 (inner diameters, inner circumferential surface areas of the tightening sections 58, and so forth in a free state) are set so as to generate frictional torques larger than the above-described respective torques $T_{J1}$, $T_{J2}$, and $T_{J3}$, thereby resisting any torque, in whichever directions of the shaft members 54 the torques act. Thus, the spring constants of the plate spring members 55 are set to be the larger for the joint J3, which is disposed on the more proximal end side.

Each of the joining members 51 includes a recessed section 53 that is tightly fitted to a boss section 52 provided in each of the link members 37 and 38 and is tiltably attached, for example, in a snap-fitting manner, to the two link members 37 and 38, thereby linking the two link members 37 and 38.

In addition, the joining member 51 is provided with a circumferential groove (wiring groove) 65 in the vicinity of, and all around, the periphery thereof. If a description is given by way of example of the joint J1, a cable 66 can be routed such that the cable 66 is guided through the cavity of the one link member 37, is extracted via the opening of the link member 37 into the circumferential groove 65 of the joining member 51, is made to run via the circumferential groove 65, and is then guided into the cavity of the other link member 38 via the opening of the other link member 38, as shown in FIGS. 4 and 5. By doing so, the cable 66 can be easily routed so as to avoid interference with the spur wheels 41 and 42.

The rotational joint K disposed on the most proximal end side of the arm section 22 includes a rotational section (not shown in the figure) that is supported rotatably relative to the body section 23, and also includes: an angle sensor (not shown in the figure), such as an encoder, for detecting the angle displacement of the rotational section relative to the body section 23; a shaft member (not shown in the figure) fixed to the rotational section; and a pair of plate spring members (not shown in the figure) that are fixed to the body section 23 and that are wound around the outer circumferential surface of the shaft member.

The frictional torque in this rotational joint K is set to have a magnitude exceeding the torque due to the weight that is applied to the rotational joint K when the arm section 22 is extended in a horizontal direction in a state where the joints J1 and J2 are extended and the joint J3 is bent to 90°.

Each of the second operating sections 20 includes: an arm rest pedestal 26 fixed to the body section 23 of the first operating section 19; and a linear-motion mechanism 27 for supporting the arm rest pedestal 26 and the first operating section 19 in an integrally movable manner. The arm rest pedestal 26 is disposed at a position at which, when the operator O grips the grip section 25 of the first operating section 19, the operator O can rest, on the arm rest pedestal 26, his or her arm near the wrist of the hand gripping the grip section 25.

The linear-motion mechanism 27 includes: a slider 28 for fixing the arm rest pedestal 26 and the first operating section 19; and a linear guide 29 for supporting this slider 28 movably in two horizontal directions orthogonal to each other, as indicated by the black arrows in FIG. 2. By moving the slider 28 in a horizontal direction with the arm resting on the arm rest pedestal 26, the position of the first operating section 19 can be moved while keeping the position/orientation at which the first operating section 19 is gripped. By doing so, the second operating sections 20 can receive operating commands via the wrists or the arms of the operator O and can generate motion commands on the basis of the forces input with the wrists or the arms working as mechanical driving forces of the two sliders 28.

The command transmission unit 21 includes: an electrical signal transmission unit 30 for connecting the first operating sections 19 and the distal-end-driving units 10; and a mechanical force transmission unit 31 for connecting the second operating sections 20 and the proximal end side moving sections 16.

The electrical signal transmission unit 30 transmits, to the control unit 4, motion commands composed of electrical signals generated by the first operating sections 19 and supplies the command signals generated by the control unit 4 to each motor of the distal-end-driving units 10. The control unit 4 calculates the amount of rotational movement and the rotational speed for each motor of the distal-end-driving units 10 on the basis of the motion commands generated by the first operating sections 19, thereby controlling each motor.

In addition, the control unit 4 controls the end effector so as to change the open/close angle of the high frequency gripper 11 according to the slide position of the slider 36 in the slide sensor 32 provided on the grip section 25 of each of the first operating sections 19. In addition, when the push buttons 33, 34, and 35 are pressed, the control unit 4 controls the functions assigned to the push buttons 33, 34, and 35, namely, the on/off state of energization in the incision mode, the on/off state of energization in the coagulation mode, and engagement/disengagement of the clutch.

The operations of the operation input device 2 and the medical manipulator system 1 according to this embodiment with the above-described structures will be described below.

In order to treat an affected area in the body of the patient P by using the medical manipulator system 1 according to this embodiment, the insertion sections 6 of the manipulators 3 are inserted into the body cavity of the patient P, and then the movable sections 9 and the elongated sections 8 are inserted into the body of the patient P through the channels R of the insertion sections 6.

Thereafter, in a state where the movable sections 9 are placed so as to be adjacent to the affected area in the body cavity, the operator O operates the operation input device 2 while checking, on the monitor 5, an image acquired by an endoscope, not shown in the figure. In order to operate the operation input device 2, the operator O grips the grip section 25 of a first operating section 19 with one of his/her hands and places the arm of his/her hand on the arm rest pedestal 26 of the second operating section 20.

Subsequently, when the operator O applies a force from his/her arm to the arm rest pedestal 26, the slider 28 to which the arm rest pedestal 26 is fixed moves in the direction of the force, and the amount of the movement is decomposed into the amount of linear movement in the forward/backward movement direction and the amount of linear movement in the left/right direction, so that the operator O can manually move, in a rough way, the distal end position of the high frequency gripper 11, located at the distal end of the movable section 9, in the forward/backward movement direction and in the left/right direction.

On the other hand, when the operator O moves the grip section 25 of the first operating section 19 gripped with his/her hand, the amount of the movement is detected by the angle sensor 47 provided in each of the joints J1, J2, J3, and K and is then transmitted to the control unit 4 as an electrical signal. In the control unit 4, an electrical motion command for moving each of the joints 12, 13, 14, and 15 of the movable section 9 so as to coincide with the angle of each of the joints J1, J2, J3, and K detected by the angle sensor 47 is calculated and is supplied to the motor connected to each of the joints 12, 13, 14, and 15. By doing so, the distal end position of the high frequency gripper 11 provided at the distal end of the movable section 9 is precisely moved in an electrically driven manner just as instructed through the movement of the hand.

Thereafter, when the operator O slides the slider 36 in the slide sensor 32 so as to grip biological tissues with the high frequency gripper 11, the control unit 4 opens or closes the high frequency gripper 11 according to the position of the slider 36. In this case, because the pointing finger of the hand of the operator O gripping the grip section 25 is disposed at a position where the pointing finger is in touch with the slider 36, the operator O can easily slide the slider 36 through the motion of the pointing finger in the longitudinal direction of the grip section 25.

In addition, when the operator O wishes to disconnect the interlinked movement between the operation input device 2 and the manipulator 3, the operator O slides his/her thumb and presses the push button 35. Because the push button 35, serving as a clutch button, is disposed at a position displaced from the position of the thumb of the operator O gripping the grip section 25, it is possible to not only prevent an incorrect operation of the clutch button but also to give a meaning to interruption of clutch operation.

Then, when the operator O releases the grip section 25 in a state where the interlinked movement between the operation input device 2 and the manipulator 3 is disconnected, the sum of the weights of the members disposed towards the distal end side from each of the joints J1, J2, J3, and K acts, as a weight driven torque for rotating each of the joints J1, J2, J3, and K, on each of the joints J1, J2, J3, and K of the arm section 22 constituting the first operating section 19 of the operation input device 2. According to the operation input device 2 of this embodiment, because each of the joints J1, J2, J3, and K is provided with the plate spring members 55 configured to generate a frictional torque that is larger than the weight driven torque and that acts in the opposite direction to that of the weight driven torque, each of the joints J1, J2, J3, and K is kept at a standstill.

Consequently, even when the operator O releases the grip section 25 in a state where the interlinked movement between the operation input device 2 and the manipulator 3 is disconnected, each of the joints J1, J2, J3, and K of the arm section 22 comes to a standstill, and the grip section 25 and the arm section 22 also come to a standstill at the current positions to keep the same positions/orientations. Because of this, the next time the operator O resumes an interlinked movement between the operation input device 2 and the manipulator 3, he/she can easily resume the interlinked movement while preventing the occurrence of a deviation between the operation input device 2 and the manipulator 3.

In addition, in this embodiment, because frictional torques resisting weight driven torques are generated by means of the shaft members 54 that are fixed to the joining members 51 and by means of the plate spring members 55 that are fixed to the link members 38, 39, and 40 and that are wound around the outer circumferential surfaces of the shaft members 54, the arm section 22 in a state where the interlinked movement is disconnected can be kept at a standstill stably with a simple structure. In particular, because a large-scale device, such as a motor, is not used, the arm section 22 can be made small.

In addition, because the pair of plate spring members 55 that are wound around each of the shaft members 54 in the opposite directions to each other are provided, a frictional torque resisting the weight driven torque is generated, in whichever direction the weight driven torque is applied, thus making it possible to stably keeping the arm section 22 in a state where the interlinked movement is disconnected at a standstill with a simple structure.

Furthermore, the frictional torque is adjusted for each of the joints J1, J2, J3, and K individually to generate a frictional torque that can resist the maximum value of the weight driven torque acting on each of the joints J1, J2, J3, and K, instead of merely producing a large frictional torque. Therefore, when the operator O operates the grip section 25, the operator O can easily move the grip section 25 with a force applied to the grip section 25.

In particular, a decrease in operability can be prevented by adjusting the frictional torques so as to move not just one but all of the joints J1, J2, J3, and K when the grip section 25 is moved with an external force that generates a torque exceeding the weight driven torque.

In addition, a mechanism configured to generate a frictional torque can be configured merely by inserting the shaft unit 48 along the longitudinal direction thereof into the insertion hole 60 provided in each of the link members 38, 39, and 40 and then fixing the shaft member 54 and a joining member 51 with the screw 56. Conversely, the shaft unit 48 can be removed from the insertion hole 60 as a whole by unfastening the screw 56 fixing the shaft member 54 to the joining member 51 and then removing the joining member 51. In other words, not only can the joints J1, J2, and J3 configured to generate frictional torques be easily assembled and disassembled but also the plate spring members 55 can be easily replaced by inserting and removing, into and from the insertion hole 60, the shaft unit 48 having the shaft member 54 and the plate spring members 55 assembled therein.

In the operation input device 2 according to this embodiment, joints having a double-joint structure are employed as examples of the three joints J1, J2, and J3 of the arm section 22. Instead of this, a joint having a single axis may be employed. In this case, it is advisable that the shaft member 54 be fixed to the one link member 37 and that the plate spring members 55 wound around this shaft member 54 be fixed to the other link member 38, if a description is given by way of example of the joint J1.

In addition, this embodiment has been described by way of an example where the plate spring members 55 serve as springy members for tightening the outer circumferential surface of the shaft member 54. Instead of this, a coil spring member that takes a cylindrical shape as a whole as a result of being formed by winding the spring member in the form of a helix may be employed.

Figure 9:
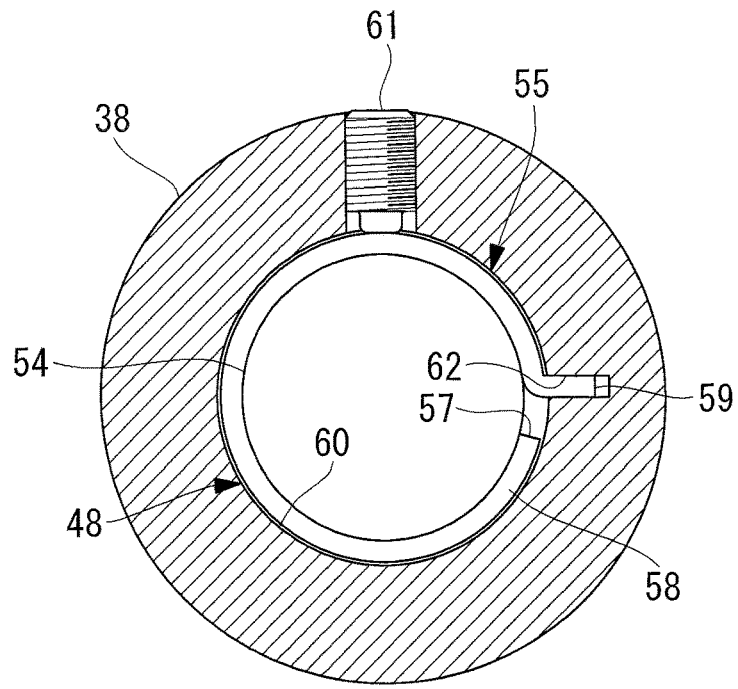
FIG. 9 is a first modification of the operation input device in FIG. 3 and is a partial transverse view of a link member showing a setscrew for adjusting a frictional torque.

In addition, a mechanism for adjusting the tightening force of the plate spring member 55 from outside, such as a setscrew (adjustment section) 61 shown in FIG. 9, may be employed. In the event that the tightening force decreases due to a change over time, the tightening force can be increased by pressing the plate spring member 55 from outside with the setscrew 61, the magnitude of the frictional torque can be adjusted with the setscrew 61 in order to keep the balance of the frictional torques generated in the plurality of joints J1, J2, and J3, and so forth.

Figure 10:
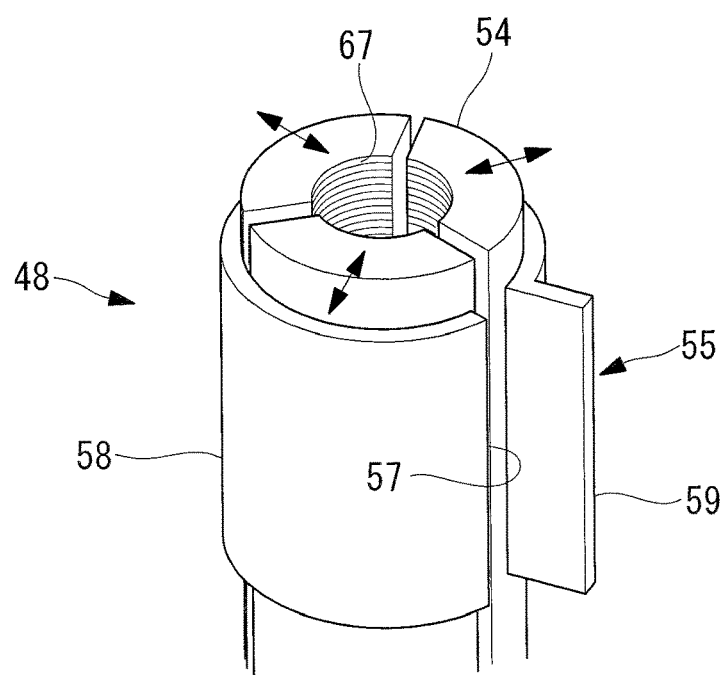
FIG. 10 is a second modification of the operation input device in FIG. 3 and is a partial perspective view of a shaft unit showing a shaft member having slots for adjusting a frictional torque and a taper female screw.

In addition, as shown in FIG. 10, a plurality of slits with a gap therebetween in the circumferential direction may be formed in the shaft member 54, and a taper female screw (adjustment section) 67 may be provided at the center, thereby making it possible to adjust, from outside, the magnitude of the frictional torque generated by the plate spring member 55 by adjusting the amount of tightening of a taper male screw (not shown in the figure) to be tightened into this taper female screw 67 to change the outer diameter of shaft member 54.

In addition, in this embodiment, the frictional torque for each of the joints J1, J2, J3, and K is adjusted with respect to the torque applied to the joint in a state where all of the joints J1, J2, and J3 of the arm section 22 are extended. Instead, the frictional torque may be adjusted such that a center (sweet spot) in the moving range of each of the joints J1, J2, J3, and K is defined so that the frictional torques that are generated in the joints J1, J2, J3, and K coincide with one another among the joints J1, J2, J3, and K when a force is applied to each of the sweet spots. By doing so, the joints J1, J2, J3, and K can be moved so as to be associated with one another while still compensating for the weight driven torques, thereby achieving a high degree of operability.

Figure 11:
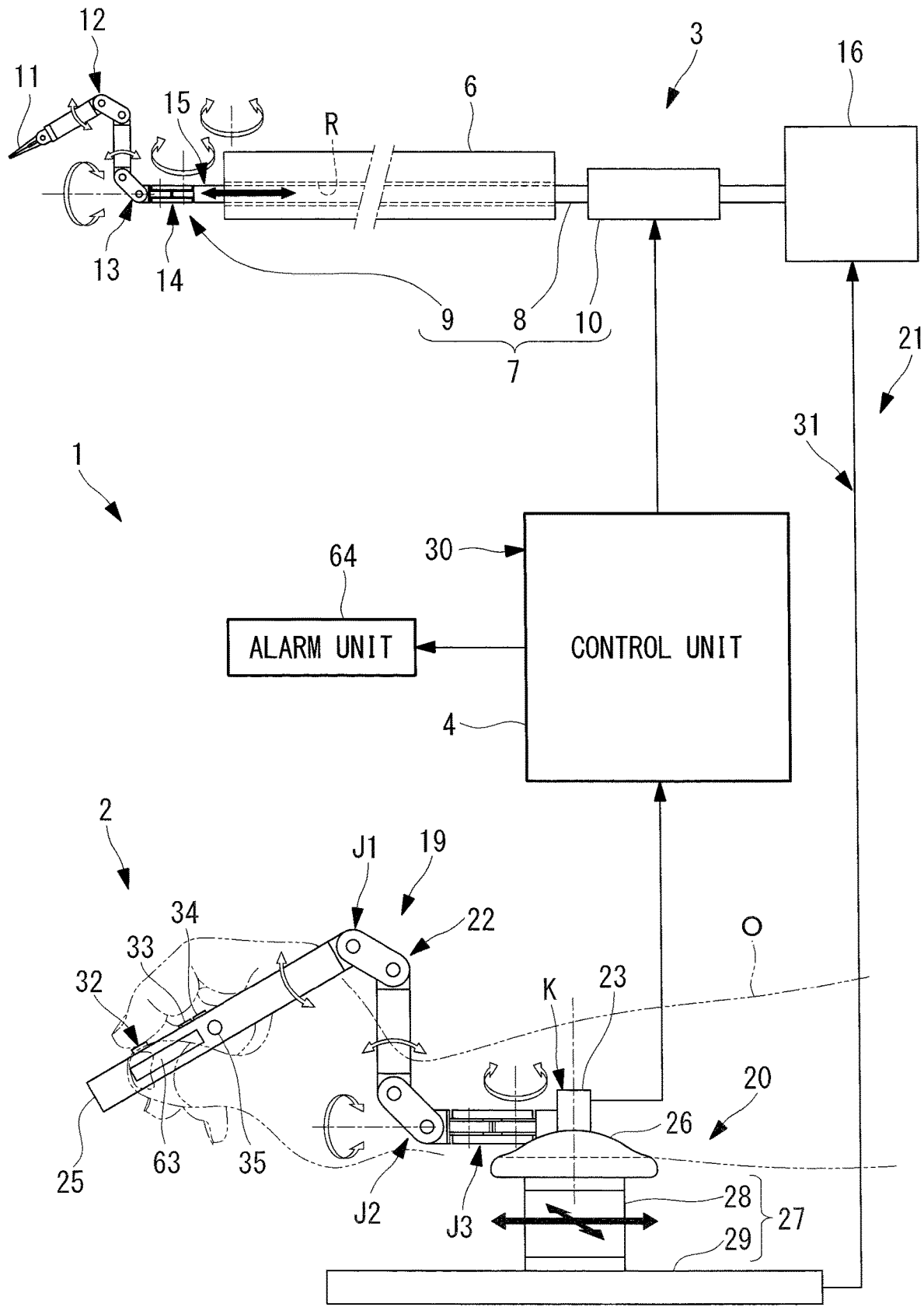
FIG. 11 is a diagram showing a modification of the medical manipulator system in FIG. 1.

In addition, as shown in FIG. 11, the grip section 25 may be provided with a contact sensor (contact detection unit) 63 that detects whether a hand of the operator O is contact therewith, so that it may be determined whether or not the relative angle displacement that is detected by the angle sensor 47 and that is sent to the control unit 4 is equal to or more than a predetermined threshold value in a state where the contact sensor 63 does not detect contact of a hand of the operator O, wherein an alarm unit 64 may be further provided in order to report that the relative angle displacement is equal to or more than the predetermined threshold value in that event. For example, when the operator O grips the grip section 25, the contact sensor 63 detects whether the thumb has come into contact therewith, at the position where the thumb of the gripping hand of the operator O is disposed.

Assuming that a description is given by way of example of the joint J1, in the event that the joint J1 moves without being capable of supporting the weight driven torque because the frictional torque generated by the springy members 55 has decreased due to, for example, a change over time, the relative angle displacement between the link members 37 and 38 is detected by the angle sensor 47, and the alarm unit 64 reports that the displacement is large in that event. By replacing the plate spring members 55 or adjusting the tightening forces generated by the plate spring members 55 on the basis of this, a deviation produced when the interlinked movement between the operation input device 2 and the manipulator 3 is disconnected can be prevented, thus making operation easy.

In addition, although the angle sensor 47 is disposed on each of the joints to detect the relative angle displacement between the link members 37, 38, 39, and 40 in this embodiment, the present invention is not limited to this. The relative angle displacement between the link members 37, 38, 39, and 40 may be detected by any other method.

An aspect of the present invention derived from the aforementioned embodiments provides an operation input device for inputting an operating command to a manipulator for observing or treating an affected area, the operation input device comprising: a grip section that is gripped by a hand of an operator; and an arm section for movably supporting the grip section, wherein the arm section includes at least two link members, and at least one joint for linking a neighboring pair of the link members so that they can tilt about a joint axis intersecting longitudinal axes thereof, and each of the joints includes a friction generation section configured to generate a fictional torque in an opposite direction to a direction in which a torque is applied.

According to this aspect, when the operator grips and moves the grip section, the external force applied to the grip section by the operator acts on the joints of the arm section as torques and changes the relative angle between at least two link members as a result of the motion of the joints. By doing so, an operating command is input to the grip section by the operator, thereby making it possible to move the manipulator on the basis of this operating command.

In this case, when a torque acts on a joint, the friction generation section generates a frictional torque in the opposite direction to the direction in which the torque is applied. More specifically, although the weights of the grip section and the arm section apply a torque to each of the joints when the operator releases the grip section, each of the joints of the arm section is kept unmoving, despite the operator not supporting the grip section, by setting the frictional torque generated by each of the friction generation sections to be larger than the maximum value of the torque caused by the weights.

Therefore, the grip section and the arm section come to a state of unmoving at their current positions and are kept at the same positions/orientations even when the operator releases the grip section in a state where the interlinked movement between the operation input device and the manipulator is disconnected. Therefore, the next time the operator resumes the interlinked movement between the operation input device and the manipulator, the operator can easily resume the interlinked movement while preventing the occurrence of a deviation between the operation input device and the manipulator.

In the above-described aspect, the friction generation section may include: a shaft member that is fixed to one of the pair of link members and that extends along the joint axis; and an springy member that is fixed to the other of the pair of link members and that is wound around an outer circumferential surface of the shaft member to tighten the shaft member radially inward.

By doing so, when an external force acts in the direction in which the relative angle between the two link members linked with the joint is changed, a torque acts between the shaft member, fixed to the one link member, and the springy member, fixed to the other link member, so as to move the two members relatively to each other in the circumferential direction of the shaft member.

Because the springy member is wound around the outer circumferential surface of the shaft member to tighten the shaft member radially inward, the static frictional force between the two members generates a frictional torque for resisting the torque caused by the external force. The springy member can generate a frictional torque that is larger than the torque caused by the gravity but that is smaller than the torque caused by an external force exceeding the gravity by appropriately adjusting the tightening force generated by the springy member. As a result, the grip section is kept unmoving when the operator releases the grip section, and the operator can easily change the position/orientation of each link member with a relatively small external force that is applied to the grip section by the operator.

In addition, in the above-described aspect, the other link member may include an insertion hole into which a shaft unit having the shaft member and the springy member wound around the outer circumferential surface of the shaft member is inserted in a longitudinal axis direction thereof, the springy member may include a substantially cylindrical tightening section that is wound around the outer circumferential surface of the shaft member, and a projecting section that extends radially outward from the tightening section, and the insertion hole may include a groove into which the projecting section is inserted in the longitudinal axis direction to engage with the shaft unit in a circumferential direction when the shaft unit is inserted into the insertion hole.

By doing so, the shaft unit, in which the projecting section of the springy member extends outward in the radial direction of the shaft member, is configured by winding the substantially cylindrical tightening section of the springy member around the outer circumferential surface of the shaft member. As the shaft unit with this structure is inserted into the insertion hole formed in the other link member along the longitudinal direction, the projecting section of the springy member is inserted into the groove provided in the insertion hole, thereby fixing the springy member so as not to move along the circumferential direction in the insertion hole of the other link member.

Because the shaft member is fixed to the one link member, a frictional torque is generated by the friction between the shaft member and the tightening section of the springy member when a torque caused by an external force is applied in a direction in which a relative angle displacement occurs between the two link members. In other words, with this structure, not only can a joint configured to generate a frictional torque be easily assembled/disassembled but also the friction member can be easily replaced by inserting and removing, into and from the insertion hole, the shaft unit having the shaft member and the springy member assembled therewith.

In addition, in the above-described aspect, the joint may include two gears that are respectively fixed to the two neighboring link members and that mesh with each other, and a joining member that is attached to each of the two link members to link the two link members such that the two link members can tilt about two parallel axes of the two respective gears, and the friction generation section includes: a shaft member that extends along the axis of the gear fixed to one of the pair of link members and that is fixed to one of the joining member and the one of the pair of link members; and an springy member that is fixed to the other of the joining member and the one of the pair of link members and that is wound around an outer circumferential surface of the shaft member to tighten the shaft member radially inward.

By doing so, the two gears fixed to the two respective link members are kept meshed with each other at all times by the joining member, and hence, when the relative angle between the two link members linked with the joint is changed, the tilting angle of the joining member relative to the one link member and the tilting angle of the other link member relative to the joining member are equal to one half of the relative angle between the two link members. In this manner, the joint constitutes a joint having a so-called double-joint structure, in which the two link members are swiveled about the two axes.

In this case, when an external force acts in the direction in which the relative angle between the two link members linked with the joint is changed, a torque acts between the shaft member, which extends along the axis of one gear and which is fixed to one of the joining member and the one of the link members, and the springy member, which is fixed to the other of the joining member and the one of the link members and which is wound around the outer circumferential surface of the shaft member, so as to move the two members relatively to each other in the circumferential direction of the shaft member.

Because the springy member is wound around the outer circumferential surface of the shaft member to tighten the shaft member radially inward, the static frictional force between the two members generates a frictional torque for resisting the torque caused by the external force. The springy member can generate a frictional torque that is larger than the torque caused by the gravity but that is smaller than the torque caused by the external force exceeding the gravity by appropriately adjusting the tightening force generated by the springy member. As a result, when a joint having a double-joint structure is used, the grip section is also kept unmoving upon the operator releasing the grip section, and the operator can easily change the position/orientation of each link member with a relatively small external force that is applied to the grip section by the operator.

In addition, in the above-described aspect, the one of the link members may include an insertion hole into which a shaft unit having the shaft member and the springy member wound around the outer circumferential surface of the shaft member is inserted in a longitudinal axis direction thereof, the springy member may include a substantially cylindrical tightening section that is wound around the outer circumferential surface of the shaft member, and a projecting section that extends radially outward from the tightening section, and the insertion hole may include a groove into which the projecting section is inserted in the longitudinal axis direction to engage with the shaft unit in a circumferential direction when the shaft unit is inserted into the insertion hole.

By doing so, also for a joint having a double-joint structure, not only can a joint configured to generate a frictional torque be easily assembled and disassembled but also the friction member can be easily replaced by inserting and removing, into and from the insertion hole, the shaft unit having the shaft member and the springy member assembled therein.

In addition, in the above-described aspect, the joining member may include a wiring groove for laying, along a route away from the gears, a cable that transmits an electrical signal between the two link members beyond the joint.

By doing so, a cable for transmitting an electrical signal can be laid along a route away from the gears provided in the joint having a double-joint structure, whereby the joint can be maintained to be sound by preventing interference between them.

In addition, in the above-described aspect, the springy member may include a pair of the tightening sections each of which increases or decreases its tightening force according to a direction of a torque applied to the shaft member, and the pair of tightening sections are arranged such that the directions with which the tightening forces increase are opposite to each other.

By doing so, one tightening section can be made to generate a frictional torque for resisting the torque in one direction, and the other tightening section can be made to generate a frictional torque for resisting the torque in the opposite direction. In this manner, the joint can be kept unmoving under the frictional torque generated by either of the tightening sections, in whichever direction a torque caused by the weight is applied to the joint. Thus, the grip section and the arm section can be kept unmoving, regardless of the positions/orientations of the grip section and the arm section when the operator releases the grip section.

In addition, in the above-described aspect, the operation input device may further include an adjustment section for adjusting the tightening force generated by the springy member.

By doing so, even if a change over time and so forth cause the tightening force generated by the springy member to decrease, the tightening force can be adjusted using the adjustment section to generate an appropriate frictional torque. In addition, in a case where a plurality of joints are provided, the operator can input a command for smooth operation when he/she grips and moves the grip section because not just one but all of the joints are moved in good balance. Therefore, the joints can be moved in good balance by adjusting the tightening forces using the adjustment sections.

In addition, in the above-described aspect, the arm section includes at least three of the link members and at least two of the joints, and a spring constant of the springy member for the joint located at a proximal end side is set greater than that of a distal end side.

In the case of a plurality of joints, a joint is subjected to a torque caused by the weights of the members disposed towards the distal end side from that relevant joint, and hence, the more proximal the position where a joint is disposed becomes, the larger the torque that is applied to the joint is. In this manner, it is possible to generate the more frictional torque for a joint that is disposed on the more proximal end side, thereby making it possible not only to keep the grip section unmoving when the operator releases the grip section but also to decrease a frictional torque to be generated for a joint on the distal end side so that the joint can make smooth movement.

In addition, in the above-described aspect, the grip section may include a contact detection unit (sensor) for detecting whether the contact detection unit is in contact with a hand of the operator, wherein the operation input device may further include: an angle sensor for detecting a relative angle displacement of each of the link members; and an alarm unit for reporting that, when the relative angle displacement detected by the angle sensor changes by a predetermined threshold value or more in a state where the contact detection unit does not detect contact with the hand of the operator, reports the same.

By doing so, in the event that a joint moves without being capable of supporting the torque caused by the weight because the frictional torque generated by the springy member has decreased due to, for example, a change over time, the relative angle displacement between the link members is detected by the angle sensor, and the alarm unit reports that a relative angle displacement more than a predetermined threshold value has occurred if so. By replacing the springy member or adjusting the tightening force generated by the springy member on the basis of this, a deviation produced when the interlinked movement between the operation input device and the manipulator is disconnected can be prevented, thus making operation easy.

In addition, in the above-described aspect, the operation input device may further include a sensor for detecting a relative angle displacement between the other link member and the joining member.

In this manner, a mechanism configured to generate a frictional torque between the one link member and the joining member is configured, and a sensor for detecting the relative angle displacement between the link members is disposed between the other link member and the joining member. Because of this, the space can be utilized efficiently, thereby making a small joint having a double-joint structure. As described above, because the relative angle displacement between each of the link members and the joining member is equal to one half of the relative angle displacement between the link members, the sensor can indirectly detect the relative angle displacement between the link members as one half thereof.

In addition, another aspect of the present invention provides a medical manipulator system including: a manipulator for observing or treating an affected area; one of the above-described operation input devices; and a control unit for controlling the manipulator on the basis of the operating command input with the operation input device.

In the above-described aspect, the manipulator may include at least one joint so as to have a joint structure similar to that of the operation input device.

According to the aforementioned aspects, there is an advantage in that it is possible to prevent a deviation between an operating section and a manipulator when they are disconnected, without having to provide a motor in each of the joints of the operating section.

REFERENCE SIGNS LIST

1 Medical manipulator system
2 Operation input device
3 Manipulator
4 Control unit (controller)
12, 13, 14, 15, J1, J2, J3, K Joint
22 Arm section (arm)
25 Grip section (grip)
37, 38, 39, 40 Link member
41, 42 Spur wheel (gear)
47 Angle sensor (sensor)
48 Shaft unit (friction generator)
51 Joining member
54 Shaft member (shaft)
55 Plate spring member (spring)
58 Tightening section
59 Projecting section
60 Insertion hole
61 Setscrew (adjustment section)
62 Groove
63 Contact sensor (contact detection unit)
64 Alarm unit
65 Circumferential groove (wiring groove)
66 Cable
67 Taper female screw (adjustment section)
O Operator

The invention claimed is:

1. An operation input device for inputting an operating command to a manipulator for observing or treating an affected area, the operation input device comprising:
a grip configured to be gripped by a hand of an operator; and
an arm comprising at least two link members and at least one joint for linking adjacent link members of the at least two link members so that the adjacent link members can tilt about a joint axis intersecting longitudinal axes of the adjacent link members, the arm movably supporting the grip,
wherein the at least one joint comprises:
a shaft fixed to one of the adjacent link members, the shaft extending along the joint axis;
a spring fixed to an other of the adjacent link members, the spring being wound around an outer circumferential surface of the shaft to tighten the shaft radially inward; and
the shaft and the spring being configured to generate a frictional torque in an opposite direction to a direction in which a torque is applied;
wherein the other of the adjacent link members comprises an insertion hole into which the shaft and the spring are inserted;
the spring comprises a substantially cylindrical tightening section that is wound around the outer circumferential surface of the shaft, the spring further comprising a projecting section that extends radially outward from the tightening section; and
the insertion hole comprises a groove into which the projecting section is inserted to engage the projecting section with the other of the adjacent link members such that the spring moves independently of the shaft.

2. The operation input device according to claim 1, wherein the spring comprises a pair of the tightening sections each of which increases or decreases its tightening force according to a direction of a torque applied to the shaft, and the pair of tightening sections are arranged such that the directions with which the tightening forces increase are opposite to each other.

3. The operation input device according to claim 1, further comprising an adjustment section for adjusting the tightening force generated by the spring.

4. The operation input device according to claim 1, wherein the at least two link members comprises at least three link members and the at least one joint comprises at least two joints, and
a spring constant of a proximal spring for a proximal joint of the at least two joints located at a proximal end side is set greater than that of a distal spring for a distal joint of the at least two joints located distally to the proximal joint.

5. The operation input device according to claim 1, wherein the grip comprises a contact sensor for detecting whether the contact sensor is in contact with a hand of the operator, and
wherein the operation input device further comprises:
an angle sensor for detecting a relative angle displacement of each of the link members; and
an alarm for reporting that the relative angle displacement detected by the sensor changes by a predetermined threshold value or more in a state where the contact sensor does not detect contact with the hand of the operator, in that event.

6. An operation input device for inputting an operating command to a manipulator for observing or treating an affected area, the operation input device comprising:

a grip configured to be gripped by a hand of an operator; and an arm comprising at least two link members and at least one joint for linking adjacent link members of the at least two link members so that the adjacent link members can tilt about a joint axis intersecting longitudinal axes of the adjacent link members, the arm movably supporting the grip, wherein the at least one joint comprises:
two gears respectively fixed to the adjacent link members, the two gears meshing with each other;
a joining member attached to each of the adjacent link members to link the adjacent link members such that the adjacent link members can tilt about two parallel axes of the two respective gears;
a shaft that extends along the axis of one of the two gears, the shaft being is fixed to one of the joining member and the one of the adjacent link members; and
a spring fixed to the other of the joining member and the one of the adjacent link members, the spring being wound around an outer circumferential surface of the shaft to tighten the shaft radially inward, wherein the shaft and spring are configured to generate a frictional torque in an opposite direction to a direction in which a torque is applied;
wherein the one of the adjacent link members comprises an insertion hole into which the shaft and the spring are inserted;
the spring comprises a substantially cylindrical tightening section that is wound around the outer circumferential surface of the shaft, the spring further comprising a projecting section that extends radially outward from the tightening section; and
the insertion hole comprises a groove into which the projecting section is inserted to engage the projecting section with the other of the joining member and the one of the adjacent link members such that the spring moves independently of the shaft.

7. The operation input device according claim 6, wherein the joining member comprises a wiring groove for laying, along a route away from the two gears, a cable that transmits an electrical signal between the adjacent link members beyond the at least one joint.

8. The operation input device according to claim 6, wherein the spring comprises a pair of the tightening sections each of which increases or decreases its tightening force according to a direction of a torque applied to the shaft, and the pair of tightening sections are arranged such that the directions with which the tightening forces increase are opposite to each other.

9. A medical manipulator system comprising:
a manipulator configured to observe or treat an affected area;
the operation input device according to claim 1; and
a controller a comprising hardware, wherein the controller is configured to control the manipulator on the basis of the operating command input with the operation input device.

10. The medical manipulator system according to claim 9, wherein the manipulator at least one joint having a joint structure similar to that of the operation input device.

11. An operation input device for inputting an operating command to a manipulator for observing or treating an affected area, the operation input device comprising:
a grip configured to be gripped by a hand of an operator; and
an arm comprising at least two link members and at least one joint for linking adjacent link members of the at least two link members so that the adjacent link members can tilt about a joint axis intersecting longitudinal axes of the adjacent link members, the arm movably supporting the grip, wherein the at least one joint comprises:
a shaft fixed to one of the adjacent link members, the shaft extending along the joint axis;
a spring fixed to an other of the adjacent link members, the spring being wound around an outer circumferential surface of the shaft to tighten the shaft radially inward; and
the shaft and the spring being configured to generate a frictional torque in an opposite direction to a direction in which a torque is applied; and
an adjustment section for adjusting the tightening force generated by the spring.

* * * * *